(12) United States Patent
Haimerl et al.

(10) Patent No.: US 8,031,922 B2
(45) Date of Patent: Oct. 4, 2011

(54) REGISTRATION OF IMAGING DATA

(75) Inventors: Martin Haimerl, Gilching (DE);
Florian Schindler, München (DE)

(73) Assignee: Brainlab AG, Feldkirchen (DE)

( * ) Notice: Subject to any disclaimer, the term of this patent is extended or adjusted under 35 U.S.C. 154(b) by 1076 days.

(21) Appl. No.: 11/842,974

(22) Filed: Aug. 22, 2007

(65) Prior Publication Data

US 2008/0049014 A1 Feb. 28, 2008

Related U.S. Application Data

(60) Provisional application No. 60/823,944, filed on Aug. 30, 2006.

(30) Foreign Application Priority Data

Aug. 22, 2006 (EP) ..................................... 06017396

(51) Int. Cl.
*G06K 9/00* (2006.01)
*G06T 15/00* (2006.01)

(52) U.S. Cl. ....................................... 382/128; 345/419

(58) Field of Classification Search .................. 382/100, 382/128–132, 285, 276, 243; 345/424, 599, 345/601, 418–419; 601/2; 606/246; 378/16, 378/19–20, 62, 207, 205, 145, 8; 250/370.08–370.09; 600/426–428, 407; 128/920, 922
See application file for complete search history.

(56) References Cited

U.S. PATENT DOCUMENTS

| | | | |
|---|---|---|---|
| 4,791,934 A | 12/1988 | Brunnett | |
| 5,951,475 A | 9/1999 | Gueziec et al. | |
| 6,470,207 B1 * | 10/2002 | Simon et al. | 600/426 |
| 7,570,791 B2 * | 8/2009 | Frank et al. | 382/132 |
| 2004/0097806 A1 | 5/2004 | Hunter et al. | |
| 2005/0259882 A1 * | 11/2005 | Dewaele | 382/243 |
| 2008/0130825 A1 * | 6/2008 | Fu et al. | 378/8 |

OTHER PUBLICATIONS

Fischer et al., "Combination of automatic non-rigid and landmark based registration: the best of both worlds", Proceedings of the SPIE—The International Society for Optical Engineering, vol. 5032, 2003, pp. 1037-1048.

Huang et al., "Hybrid Image Registration based on Configural Matching of Scale-Invariant Salient Region Features", Proceedings of the 2004 IEEE Computer Society Conference on Computer Vision and Pattern Recognition Workshops, Jun. 2004, pp. 1-10.

Johnson et al., "Consistent Landmark and Intensity-Based Image Registration", IEEE Transactions on Medical Imaging, vol. 21, No. 5, May 2002, pp. 450-452.

Russakoff et al., "Intensity-Based 2D-3D Spine Image Registration Incorporating One Fiducial Marker", Lecture Notes in Computer Science; Medical Image Computing and Computer-Assisted Intervention, vol. 2878, No. Part 1, 2003, pp. 287-294.

* cited by examiner

*Primary Examiner* — Samir Ahmed
*Assistant Examiner* — Mehdi Rashidian
(74) *Attorney, Agent, or Firm* — Renner, Otto, Boisselle & Sklar, LLP

(57) ABSTRACT

A method of determining in a three-dimensional operating space a measure of super-imposition M between at least a portion of an object and a spatial representation of the object or part thereof in an object representation pose, a pose comprising position and orientation in operating space includes:

a) obtaining a similarity measure S between a first imaging data taken in first respective imaging poses of the object or part thereof and second imaging data comparable to the first imaging data taken in second respective imaging poses that are digitally reconstructed from the spatial representation of the object or part thereof in the object representation pose;

b) locating in operating space at least one point on the surface of the object or part thereof;

c) obtaining a distance measure D between the at least one point in operating space and a surface of the spatial representation of the object or part thereof in the object representation pose; and d) obtaining a measure of superimposition M by a combination of the similarity measure S and the distance measure D.

14 Claims, 2 Drawing Sheets

REGISTRATION OF IMAGING DATA

RELATED APPLICATION DATA

This application claims priority of U.S. Provisional Application No. 60/823,944 filed on Aug. 30, 2006, which is incorporated herein by reference in its entirety.

FIELD OF THE INVENTION

The present invention relates to registration systems and, more particularly, to a method and apparatus for registering a surgical object and/or a spatial representation of the object in three-dimensional space.

BACKGROUND OF THE INVENTION

Spatial representations of a body or body portions of a patient are indispensable in computer-assisted surgery (CAS), for instance. Imaging means available to date, however, such as computer tomography (CT) and magnetic resonance imaging (MRI), are more suited for preoperative imaging, and less suited for use during surgery. It is therefore a general custom to acquire spatial representations comprising serial sections acquired from CT or MRI scans prior to surgical interventions.

For example, during surgery the patient or portions of interest of the patient may be brought into alignment with pre-operatively acquired spatial representations of the patient or portions of the patient. In particular, two-dimensional imaging techniques may be applied to match or register an object, the body of a patient or a body portion of a patient, for instance, to pre-operatively acquired spatial representations of the object.

U.S. Pat. No. 4,791,934 (Brunnett) describes a system wherein the current actual position of a patient and diagnostic data comprising a spatial representation of a body portion of the patient are brought into registration by taking two-dimensional radiographic reference images of a body portion of interest from a selected spatial position and angular orientation (pose) of a radiographic imaging apparatus. Subsequently, a shadowgraphic image synthesizer may be used to synthesize analogous shadowgraphic images from the diagnostic data forming a spatial representation of the body portion of interest. The synthetic images are taken from the same spatial position and angular orientation (pose) as the reference images. By adjusting the spatial position and angular orientation (pose) of the synthetic camera, an optimal match between the superimposed reference and synthetic images can be achieved. From the adjusted spatial position and angular orientation (pose) of the synthetic camera, the pose of the spatial representation of the body portion of interest can be adjusted accordingly and, thus, be brought into alignment with the actual position of the patient.

In "A Comparison of Similarity Measures for Use in 2-D-3-D Medical Image Registration", IEEE Transactions on Medical Imaging, Vol. 17, No. 4, August 1998, Penney et al. describe alignment techniques to register pre-operative three-dimensional CT scans forming spatial representations of an object to intra-operatively acquired two-dimensional X-ray fluoroscopy images. By casting rays through a CT volume, integrating values derived from the volume elements (voxels) of the CT scan along the ray, and projecting them onto an imaging plane, digitally reconstructed radiographs (DRRs) can be produced that may resemble a radiograph. Penney et al. continue to describe various similarity measures between fluoroscopic reference images of an object and digitally reconstructed radiographs (DRRs) of a spatial object representation based on normalized cross-correlation of image pairs, on normalized cross-correlation of gradient filtered image pairs, and on entropy evaluation in a difference image between image pairs, for instance.

U.S. Pat. No. 5,951,475 (Gueziec et. al) describes a system for registering two-dimensional fluoroscopic images with a three-dimensional model of a surgical tissue of interest, without using digitally reconstructed radiographs (DRRs). Instead, a bundle-adjustment technique is implemented using contours detected in the two-dimensional fluoroscopic images.

In "Intensity-Based 2D-3D Spine Image Registration Incorporating one Fiducial Marker", MICCAI 2003, pp. 287-294, 2003, Russakoff et al. propose the usage of an additional fiducial marker for the registration of a three-dimensional computed tomography (CT) image to one or more two-dimensional X-ray projection images. This method requires the implantation of a marker in the patient. An implanted fiducial marker is used as an additional pair point or corresponding point for the registration. An image similarity measure and a point distance are additively combined as an optimization measure for the registration. However, the additive combination of image similarity values and distance values within the optimization measure is not independent of the scaling of grey-level intensity values in the X-ray projection images. Thus, the registration procedure according to Russakoff et al. depends on variations in the image quality.

In conventional 2D/3D registration of the pelvis, for instance, two fluoroscopic images are typically acquired. With known techniques, minor directional errors in the alignment of the pubis may lead to significant errors in the acetabulum and spina region. In order to be suited to hip surgeries, for instance, very accurate registration, especially in these areas, is required.

SUMMARY OF THE INVENTION

A method and system for registering pre-operatively acquired three-dimensional patient data with an actual position of the patient in the operating room dispenses entirely with the use of fiducial markers, which hitherto have been employed to improve registration accuracy. A fiducial marker may be a metallic element usually implanted in bone regions of a patient, and typically requires a surgical implantation procedure. In contrast to known methods, the inventive method and system disclosed herein does not require the implantation of such markers.

The inventive method uses an additional constraint, which can significantly improve the accuracy as well as the robustness of the registration of an object in an operating room to a data representation of the object. The additional constraint for the registration can be obtained by acquiring, in a three-dimensional coordinate system (preferably a Cartesian coordinate system) related to the operating environment, a location of at least one point on the surface of a bone region, for instance, which may be the spina or acetubulum region. Since these regions cover relatively large areas, rotational errors may be largely reduced.

The inventive method can integrate the surface-based information into 2D-3D-registration techniques (in particular matching of CT-fluoroscopic images). An object can be registered by means of acquired 2D image data and 3D image data (e.g., fluoroscopic images and a 3D CT scan) and one or more additional surface points. The object to be registered may be a patient or body portions of a patient in diagnostic, therapeutic, clinical or automatic examination or treatment.

The inventive method can integrate surface-based information registration techniques based on imaging data, e.g., 2D-3D-registration techniques (in particular matching of CT-fluoroscopic images). An object can be registered by means of the operatively acquired 2D image data and into operatively acquired 3D image data (e.g., fluoroscopic images and a 3D CT scan) and one or more additional surface points.

Prior to acquiring a surface point or surface points on a bone region of the patient, for instance, the patient may be immobilized. Alternatively, relative movements or locations of the patient may be acquired by a position sensing system or a navigation system. These relative locations then may be taken into account in the registration method and system described herein by accordingly adjusting the position and orientation (pose) of the spatial data representing the patient.

In a method for use in a three-dimensional operating space, a measure of super-imposition M between an object or a portion thereof, referred to as object, and a spatial representation of the object, referred to as object representation, in an object representation pose, a pose comprising position and orientation in operating space, may comprise:

a) obtaining a similarity measure S between the first imaging data taken in first respective imaging poses of the object and second image data comparable to the first imaging data taken in second respective imaging poses which are digitally reconstructed image data from the object representation in the object representation pose,
b) locating in operating space at least one point on the surface of the object; and
c) obtaining a distance measure D between the at least one point in operating space and a surface of the object representation in the object representation pose, wherein the method further comprises:
obtaining a measure of superimposition M by a combination of the similarity measure S and the distance measure D which may be scale invariant at least with respect to the similarity measure S.

A method of registering in a three-dimensional operating space an object or a portion thereof, referred to as object, and a spatial representation of the object, referred to as object representation, in an object representation pose, a pose comprising position and orientation in operating space, may comprise:

a) taking in first respective imaging poses first image data of the object;
b) taking in second respective imaging poses second image data comparable to the first imaging data which are digitally reconstructed from the object representation in the object representation pose;
c) obtaining a similarity measure S between the first and second image data;
d) locating in operating space at least one point on the surface of the object;
e) obtaining a distance measure D between the at least one point and a surface of the object representation in the object representation pose;
f) obtaining a measure of superimposition M by a combination of the similarity measure S and the distance measure D which may be scale invariant at least with respect to the similarity measure S;
g) jointly performing step h) and repeating steps b), c), e), and f) a predetermined number of times or until two consecutive measures of superimposition M obtained in step f) approach one another up to a predetermined threshold;
h) changing the object representation pose to a different pose relative to the second respective imaging poses.

An apparatus for use in a three-dimensional operating space such as an object or a portion thereof, referred to as object, and a spatial representation of the object, referred to as object representation, in an object representation pose, a pose comprising position and orientation in operating space, the apparatus comprises:

a first device for taking in first respective imaging poses first imaging data of the object;
a second device for taking in second respective imaging poses second imaging data comparable to the first imaging data which are digitally reconstructed from the object representation in the object representation pose;
a third device for obtaining a similarity measure S between the first and second imaging data;
a fourth device for locating in operating space at least one point on the surface of the object;
a fifth device for obtaining a distance measure D between the at least one point and a surface of the object representation in the object representation pose;
a sixth device for obtaining a measure of superimposition M by a combination of the similarity measure S and the distance measure D which may be scale invariant at least with respect to the similarity measure S;
a seventh device for changing the object representation pose to a different pose relative to the second respective imaging poses and
an eighth device for determining whether two consecutive measures of superimposition M for different poses of the object representation obtainable from the sixth device approach one another up to a predetermined threshold.

In the method and system described herein, the similarity measure S and the distance measure D may be combined to a measure of superimposition M as $$M=S/(a+D),$$

wherein "a" is a predetermined constant.

Scale invariance at least with respect to the similarity measure S may comprise scale invariance in ordering relations between measures of superimposition M at least with respect to the similarity measure S.

Further, relative locations of the object may be acquired via a pointer attached to the object by means of a position sensing or a navigation system, for instance, and the pose of the object representation may be adapted accordingly.

The spatial representation of the object may comprise a decision rule and plurality of volume elements, referred to as voxels, piled up in slices comprising rows and columns, each voxel carrying at least one value, and the decision rule determining the membership of each voxel to the object in accordance with the at least one value of the voxel.

Voxels may be obtained from imaging devices using computed tomography (CT), magnetic resonance (MR), single photon emission computed tomography (SPECT), or positron emission tomography (PET).

Reference image data taken of the object or portions of the object comprise imaging data, e.g., ultrasound or fluoroscopy radiographs, which may be compared with digitally reconstructed imaging data, e.g., digitally reconstructed radiographs (DRRs). Imaging poses of the reference radiographs preferably assume essentially the same positions and orientations relative to each other as the respective imaging process of the reconstructed imaging data, e.g., DRRs. Further, the geometry of the imaging device or devices used to take the reference radiographs preferably is essentially identical to the geometry of the virtual or synthetic imaging devices used to take the reconstructed imaging data.

The similarity measure S between the first and second image data may be obtained by correlating corresponding pairs of first and second imaging data, and/or wherein the distance measure D between the at least one point and a surface of the object representation in its pose may be obtained by the Euclidean distance of the point and the surface of the object representation in the case of a single point and otherwise by averaging the Euclidean distances of more than one point and the surface of the object representation. A point or points on the surface of the object may be located using a position sensing system or a navigation system.

The method described herein may further be executed by a computer program executed on a general purpose computer, a dedicated computer or a computer on a chip (SOC). Further, the computer may be caused to function as the apparatus described herein via a computer program. The computer program for executing the method and/or the computer program causing a computer to function according to the apparatus may be stored on a computer-readable data carrier.

BRIEF DESCRIPTION OF THE DRAWINGS

The forgoing and other features of the invention are hereinafter discussed with reference to the drawing.

DETAILED DESCRIPTION

Figure 1:
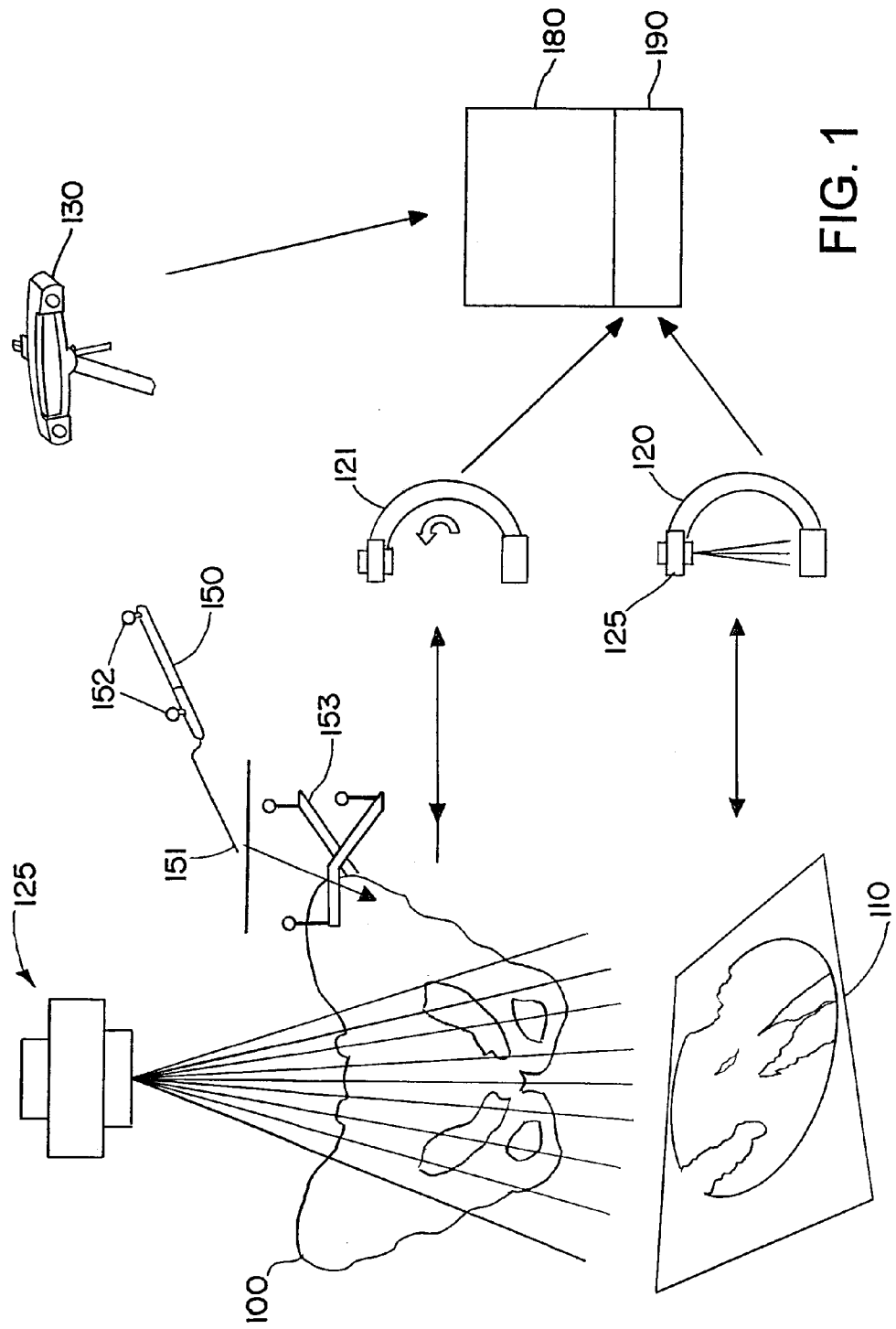
FIG. 1 is a schematic representation illustrating an application of an exemplary method in accordance with the invention for registering an object or a portion of an object to a spatial representation of the object or a portion of the object.

FIG. 1 shows in diagrammatic form a portion of an object 100, for instance the pelvis of a patient. A spatial representation (not shown) may have been pre-operatively acquired by means of a computer tomograph 121 and stored in a computer system 180. During surgery, two-dimensional fluoroscopic images 110 may be acquired by an imaging system 120 comprising an X-ray source 125. Alternatively, other imaging data may be acquired by suitable imaging means such as ultrasound images, for example. The imaging system 120 may be navigated (e.g., its positional and orientational locations in the operating room (not shown) may be controlled and/or registered by the computer system 180). Alternatively, the imaging system 120 may comprise active or passive elements indicative of a position of the imaging system 120, and observed by one or more cameras 130 that may be operatively coupled to the computer system 180. A marker 153 may be used to acquire relative locations of the object by means of the position sensing system 130, for instance.

In addition to the fluoroscopic images 110 taken by the imaging system 120, a pointer 150 comprising a tip 151 and position signalling elements 152 that can be tracked by means of the at least one camera 130. A point or points on the surface of the object, for instance on the surface of the pelvis 100 of the patient, can be located by means of guiding the tip of the pointer 150 to a desired position or positions. A tracking system comprising the pointer 150 and the at least one camera 130 can determine the location of the indicated point or points in three-dimensional coordinate system related to the operating environment.

A registration method 190 as described herein may be executed by means of the computer system 180. The registration can be computed by a known optimization technique that optimizes a given optimization measure. The parameters for optimization can be specified by a relation between the 2D domain and the 3D domain. After fluoroscopic images 110 have been taken with a X-ray/fluoroscopic imaging device 120, for instance, and surface points on the surface of the object have been taken, the corresponding data can be stored in the computer system 180.

In the computer system 180, digitally reconstructed radiographs (DRRs) can be generated and stored from a spatial representation of the object (not shown), which also can be stored in the computer system 180, and on the position and orientation of the X-ray source 125 of the imaging system 120 (which also can be stored in the computer system 180). Next a similarity measure S between the X-ray/fluoroscopic images 110 and the digitally reconstructed radiographs (not shown) can be obtained by means of instructions executed in the computer system 180, for instance.

Subsequently, a distance measure D between the at least one point acquired on the surface of the object in a three-dimensional coordinate system related to the operating environment and a surface of the object representation (not shown) can be obtained by taking into account the current position and orientation (pose) of the spatial representation of the object (not shown). Then, the similarity measure S and the distance measure D are combined to a similarity measure S, for example, according to Equation 1, where "a" is a predetermined constant.

$$M=S/(a+D) \qquad \text{Equation 1}$$

The inventive combination of the similarity measure S, e.g., a CT-fluoroscopic optimization measure, and the distance measure D, e.g., a surface distance term, uses in one embodiment a multiplicative combination of S and D. Due to the combination of S and D to a measure of superimposition M, an optimization with respect to the measure of superimposition M is scale invariant with respect to a preferable, montotoneus function f (D), where f (D)=1/(const+D), for instance. Both S and 1/(a+D) positively assess favorable positions and/or orientations. In particular, the inventive method yields an invariance with respect to the scaling of grey levels in the fluoroscopic images as well as in the CT data of the spatial representation of the object.

Usually a standardized scaling for the image intensity values is not available. Therefore, it is desirable to provide a scale invariant optimization procedure with respect to the similarity term S. For this purpose, a multiplicative combination of S and D can be provided by the inventive method and system.

Depending on the value of the measure of superimposition M obtained as described above, the position and orientation (pose) of the object representation may be charged or adjusted to assume a different position and/or orientation in the three-dimensional coordinate system related to the operating environment. Alternatively, it might be convenient for a user of the inventive method and system to adjust the position and orientation (pose) of a virtual or synthetic camera by means of which the digitally reconstructed radiographs (DRRs) are taken. In this embodiment, the pose of the spatial representation of the object will be changed according to the change of the pose of the virtual or synthetic camera that is used to take the digitally reconstructed radiographs (not shown).

Figure 2:
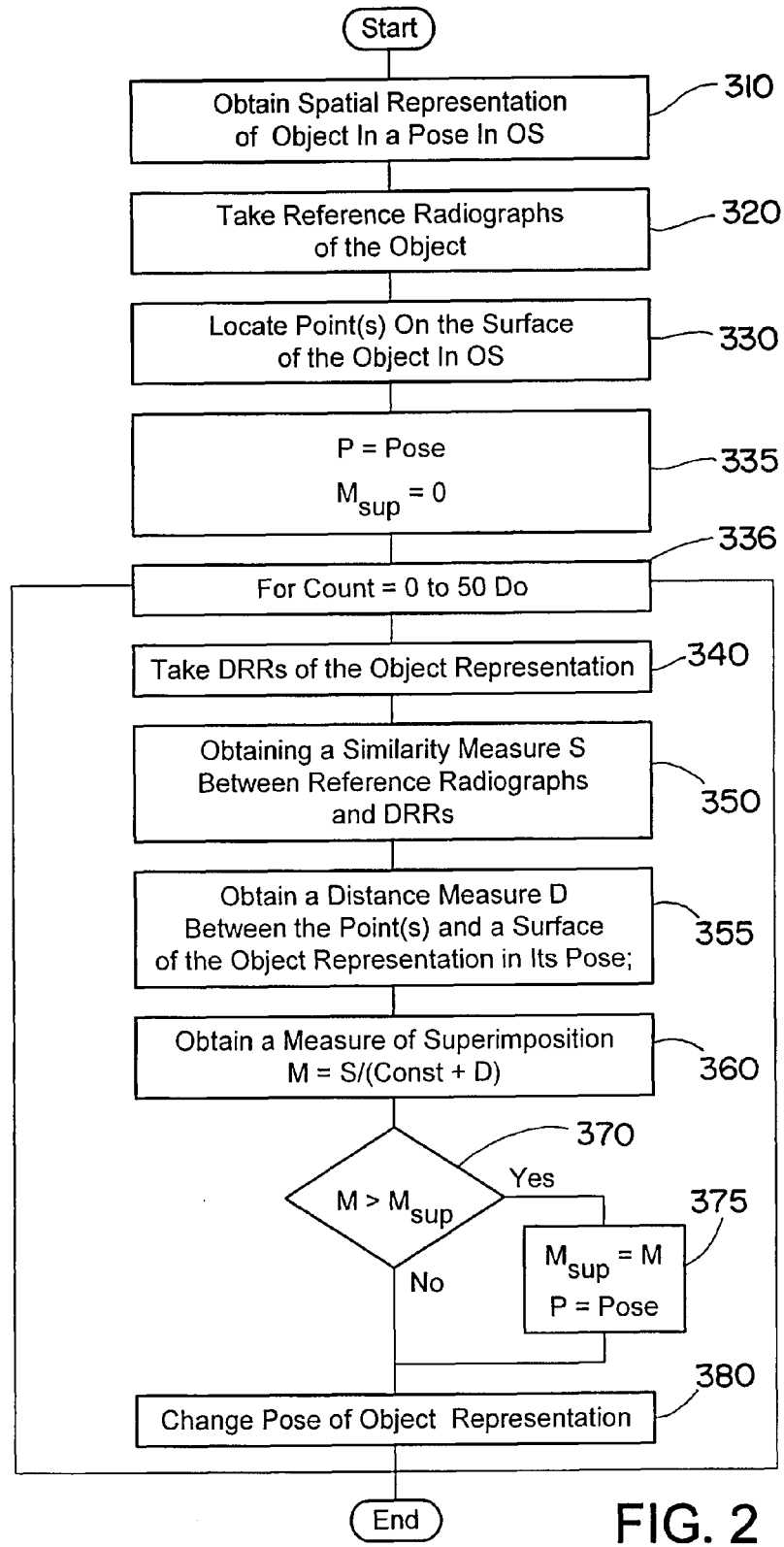
FIG. 2 is a flowchart of an exemplary method in accordance with the invention.

Referring now to FIG. 2, a flow diagram shows the general principle used in the registration system of FIG. 1 or in the method for registering an object or a portion of an object and a spatial representation of the object or a portion of the object in three-dimensional space. In the exemplary flow diagram, a spatial representation of the object or a portion of the object is assumed to be in a known initial position and orientation (pose) related to the operating environment.

Beginning at step 310, it is assumed that a spatial representation of the object in a known position and orientation (pose) in a three-dimensional operating space has been acquired preoperatively. Next in step 320, reference image data, for example radiographs of the object are taken, for example, with a navigated X-ray/fluoroscopic imaging system as shown in FIG. 1.

Subsequently a point or a number of points is/are located at step 330 on the surface of the object in operating space. For simplicity, the embodiment of the registration method shown in FIG. 2 incorporates a straight forward optimization procedure that, starting from an initial pose of the object representation, obtains an optimal pose P as the pose with the biggest value of the measure of superimposition M, which is obtained in a predetermined number of iterations of steps 340 to 380 as discussed below.

At step 335, before the iteration begins, P and $M_{sup}$ are initialized. A predetermined number of iterations are set at step 336 (e.g., a counter is initialized and then incremented each time an iteration is completed, and the counter is compared to a preset value to determine if additional iterations will be performed). In each iteration, reconstructed imaging data, for example digitally reconstructed radiographs (DRRs) of the object representation in the current pose, can be obtained by casting rays through the spatial object representation and integrating the volume elements hit by any ray to form reconstructed radiograph, as indicated at step 340.

At step 350, a similarity measure S is obtained between the reference image data and the digitally reconstructed image data (DRRs) of the previous step. Then at step 355, a distance measure D is obtained between one or more points and a surface of the object representation in its current pose.

The object may be represented by a decision rule and a plurality of volume elements (voxels) piled up in slices comprising rows and columns, each voxel carrying at least one value, and the decision rule determining the membership of each voxel to the object in accordance with the at least one value of the voxel. In such a representation of an object or a portion of an object, a surface of the object representation may be obtained by threshholding the value or value of each voxel at a pre-determined value. Using known techniques, a distance between a point in operating space and surface voxels of the object representation may be obtained with sub-voxel accuracy.

At step 360, the similarity measures S and the distance measure D are combined to a measure of superimposition M=S/(const+D). Then at step 370, it is determined whether the measure of superimposition M exceeds the current maximum $M_{sub}$ and if so, the optimized pose P is set to the current pose and the maximum measure of superimposition $M_{sub}$ is set to the current measure of superimposition M at step 375.

In the case where the current measure of superimposition M does not exceed the maximum value $M_{sub}$, or after completion of the updating step 375, the current pose of the object representation is changed to a different position and orientation. Then the optimizing iteration controlled by the count at step 336 is continued, and steps step 340 to 380 are repeated until the desired number of iterations have been completed.

In each step of the iteration or optimization, artificial images may be rendered from the 3D data set (according to the current pose or parameter settings) and compared with the 2D data set. After completing a pre-determined number of iterations, the registration procedure is terminated, resulting in a pose P that registers the object representation with an actual position of the object in operating space.

Alternative convergence criteria for terminating the iteration of steps 340 to 380 may comprise the determination whether the measure of superimposition M in a given iteration exceeds a predetermined threshold.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of determining in a three-dimensional operating space a measure of super-imposition M between at least a portion of an object and a spatial representation of the object or part thereof in an object representation pose, a pose comprising position and orientation in operating space, the method comprising:
   a) obtaining a similarity measure S between a first imaging data taken in first respective imaging poses of the object or part thereof and second imaging data comparable to the first imaging data taken in second respective imaging poses that are digitally reconstructed from the spatial representation of the object or part thereof in the object representation pose;
   b) locating in operating space at least one point on the surface of the object or part thereof, said locating including using data obtained from a pointer guided to a location on the surface of the object without said pointer being attached to the object;
   c) obtaining a distance measure D between the at least one point in operating space and a surface of the spatial representation of the object or part thereof in the object representation pose; and
   d) obtaining a measure of superimposition M by a combination of the similarity measure S and the distance measure D.

2. The method according to claim 1, further comprising inter-operatively acquiring the first imaging data and/or reconstructing the second imaging data from a pre-operatively acquired object representation.

3. The method according to claim 1, wherein the combination of the similarity measure S and the distance measure D includes a combination that is scale invariant at least with respect to the similarity measure S.

4. A method of determining in a three-dimensional operating space a measure of super-imposition M between at least a portion of an object and a spatial representation of the object or part thereof in an object representation pose, a pose comprising position and orientation in operating space, the method comprising:
   a) obtaining a similarity measure S between a first imaging data taken in first respective imaging poses of the object or part thereof and second imaging data comparable to the first imaging data taken in second respective imaging poses that are digitally reconstructed from the spatial representation of the object or part thereof in the object representation pose;

b) locating in operating space at least one point on the surface of the object or part thereof;

c) obtaining a distance measure D between the at least one point in operating space and a surface of the spatial representation of the object or part thereof in the object representation pose; and d) obtaining a measure of superimposition M by a combination of the similarity measure S and the distance measure D, wherein the combination of the similarity measure S and the distance measure D includes a combination that is scale invariant at least with respect to the similarity measure S, and wherein scale invariance at least with respect to the similarity measure S comprises scale invariance in ordering relations between measures of superimposition M at least with respect to the similarity measure S.

5. A method of determining in a three-dimensional operating space a measure of super-imposition M between at least a portion of an object and a spatial representation of the object or part thereof in an object representation pose, a pose comprising position and orientation in operating space, the method comprising:

a) obtaining a similarity measure S between a first imaging data taken in first respective imaging poses of the object or part thereof and second imaging data comparable to the first imaging data taken in second respective imaging poses that are digitally reconstructed from the spatial representation of the object or part thereof in the object representation pose;

b) locating in operating space at least one point on the surface of the object or part thereof;

c) obtaining a distance measure D between the at least one point in operating space and a surface of the spatial representation of the object or part thereof in the object representation pose; and d) obtaining a measure of superimposition M by a combination of the similarity measure S and the distance measure D, wherein obtaining the measure of superimposition M by the combination of the similarity measure S and the distance measure D includes using $M=S/(a+D)$ to obtain the superimposition M, wherein "a" is a predetermined constant.

6. The method according to claim 1, further comprising: acquiring relative locations of the object, and adapting the object representation pose based on the acquired relative locations.

7. The method according to claim 6, wherein acquiring the relative locations of the object includes using a position sensing system or a navigation system to detect a marker fixedly attached to the object.

8. The method according to claim 1, wherein the object is a body of a patient.

9. The method according to claim 1, wherein the spatial representation of the object or part thereof comprises a decision rule and plurality of volume elements are arranged in slices comprising rows and columns, each volume element carrying at least one value, and the decision rule determining the membership of each volume element to the object in accordance with the at least one value of the volume element.

10. The method according to claim 9, further comprising obtaining the volume elements from imaging the object or part thereof using at least one of computed tomography (CT), magnetic resonance (MR), single photon emission computed tomography (SPECT), or positron emission tomography (PET).

11. The method according to claim 1, wherein the first imaging data comprise ultrasound images or fluoroscopy radiographs, and the second imaging data comprise digital reconstructed images or digitally reconstructed radiographs (DRRs), wherein the first respective imaging poses assume essentially the same position and orientations relative to each other as corresponding second imaging poses.

12. The method according claim 1, wherein locating in operating space at least one point on the surface of the object or part thereof includes using a position sensing system or a navigation system to locate the at least one point on the surface of the object or part thereof.

13. A computer program embodied on a non-transitory machine readable medium for determining in a three-dimensional operating space a measure of super-imposition M between at least a portion of an object and a spatial representation of the object or part thereof in an object representation pose, a pose comprising position and orientation in operating space, the computer program comprising:

a) code that obtains a similarity measure S between a first imaging data taken in first respective imaging poses of the object or part thereof and second imaging data comparable to the first imaging data taken in second respective imaging poses that are digitally reconstructed from the spatial representation of the object or part thereof in the object representation pose;

b) code that locates in operating space at least one point on the surface of the object or part thereof, said code that locates including code that uses data obtained from a pointer guided to a location on the surface of the object without said pointer being attached to the object;

c) code that obtains a distance measure D between the at least one point in operating space and a surface of the spatial representation of the object or part thereof in the object representation pose; and d) code that obtains a measure of superimposition M by a combination of the similarity measure S and the distance measure D.

14. The method according to claim 1, wherein locating in operating space at least one point on the surface of the object includes locating the at least one point without using data obtained from a marker attached to the object.

* * * * *